(12) United States Patent
Caspersen

(10) Patent No.: US 8,362,446 B1
(45) Date of Patent: Jan. 29, 2013

(54) APPARATUS FOR DETERMINING THE POSITION OF AN OBJECT

(75) Inventor: Christian Caspersen, Nivå (DK)

(73) Assignee: 2C A/S, Niva (DK)

( * ) Notice: Subject to any disclaimer, the term of this patent is extended or adjusted under 35 U.S.C. 154(b) by 1061 days.

(21) Appl. No.: 09/806,457

(22) PCT Filed: Sep. 30, 1999

(86) PCT No.: PCT/DK99/00515
§ 371 (c)(1),
(2), (4) Date: Jun. 14, 2001

(87) PCT Pub. No.: WO00/20838
PCT Pub. Date: Apr. 13, 2000

(30) Foreign Application Priority Data

Oct. 1, 1998  (DK) .................................. 1998 01243

(51) Int. Cl.
*G01N 21/64* (2006.01)
(52) U.S. Cl. ...................................... 250/458.1; 356/73
(58) Field of Classification Search ............... 250/458.1; 356/73
See application file for complete search history.

(56) References Cited

U.S. PATENT DOCUMENTS

| | | | | |
|---|---|---|---|---|
| 3,696,385 A | * | 10/1972 | Burns ............................ | 340/316 |
| 3,963,351 A | * | 6/1976 | Chance et al. ................. | 356/317 |
| 4,601,537 A | * | 7/1986 | Saccocio ........................ | 385/116 |
| 4,744,663 A | * | 5/1988 | Hamashima et al. ......... | 356/615 |
| 4,758,727 A | | 7/1988 | Tomei et al. | |
| 5,224,144 A | | 6/1993 | Annis | |
| 5,377,002 A | * | 12/1994 | Malin et al. ................. | 356/237.2 |
| 5,381,224 A | * | 1/1995 | Dixon et al. .................... | 356/72 |
| 5,479,252 A | * | 12/1995 | Worster et al. ............. | 356/237.5 |
| 5,656,429 A | | 8/1997 | Adelman | |
| 5,846,452 A | * | 12/1998 | Gibbons et al. ............ | 252/299.4 |
| 5,892,577 A | * | 4/1999 | Gordon ........................... | 356/73 |

(Continued)

FOREIGN PATENT DOCUMENTS

| | | |
|---|---|---|
| EP | A 392475 | 10/1990 |
| GB | A1 388107 | 3/1975 |
| GB | A2 243681 | 11/1991 |
| WO | A 9609548 | 3/1996 |

(Continued)

OTHER PUBLICATIONS

Ekins et al. Multianalyte microspot immunoassay-microanalytical "compact disk" of the future, Clinical Chemistry, vol. 37, No. 11 (1991), pp. 1955-1967.*

*Primary Examiner* — David Porta
*Assistant Examiner* — Shun Lee
(74) *Attorney, Agent, or Firm* — Gifford, Krass, Sprinkle, Anderson & Citkowski, P.C.

(57) ABSTRACT

The present invention relates to a method and apparatus which can provide rapid scanning of large specimens (14) to detect and determine positions of objects having specific characteristics. The apparatus may, further, be adapted to store information associated with the positions of the detected objects and to retrieve this position information so that an operator may locate a particular type of target object or objects in the specimen for detailed inspection and analysis subsequent to the scanning. The position information may be stored in a volatile or non-volatile memory device provided therefore in a preferred embodiment of the invention. The specimen may be provided on a solid support, such as a circular disc (13) which may be rotatably mounted about an axis (17) of a frame of the apparatus. The objects can be cells or microorganisms of a particular rare type, i.e. they may be present in a very low density in the specimen.

19 Claims, 1 Drawing Sheet

U.S. PATENT DOCUMENTS

| | | | | |
|---|---|---|---|---|
| 5,912,257 | A | * | 6/1999 | Prasad et al. .................. 514/356 |
| 6,049,421 | A | * | 4/2000 | Raz et al. ....................... 359/394 |
| 6,110,748 | A | * | 8/2000 | Reber et al. ....................... 435/6 |
| 6,188,132 | B1 | * | 2/2001 | Shih et al. ..................... 257/724 |
| 6,342,349 | B1 | * | 1/2002 | Virtanen ........................... 435/6 |

FOREIGN PATENT DOCUMENTS

| | | | |
|---|---|---|---|
| WO | WO 98/12559 | * | 3/1998 |
| WO | 9825131 | | 6/1998 |
| WO | A 9907897 | | 2/1999 |

* cited by examiner

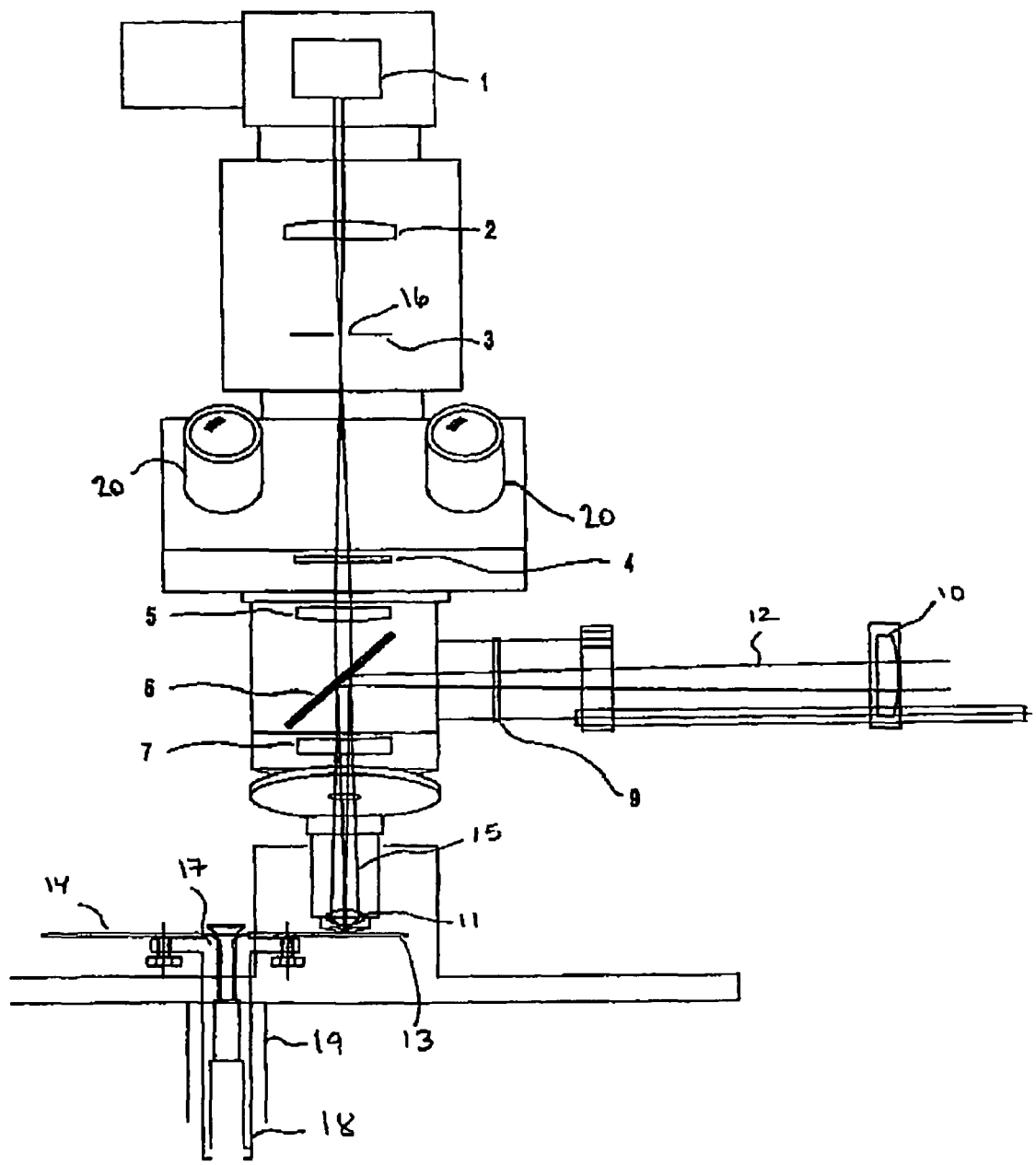

APPARATUS FOR DETERMINING THE POSITION OF AN OBJECT

This application is the national phase under 35 U.S.C. §371 of PCT International Application No. PCT/DK99/00515 which has an International filing date of Sep. 30, 1999, which designated the United States of America.

FIELD OF THE INVENTION

The present invention relates to a method and an apparatus that provide rapid scanning of large specimens to detect and determine positions of objects having specific characteristics. The apparatus may, further, be adapted to store information associated with the positions of the detected objects and also adapted to identify the objects. The positions of the objects and/or their identities may be stored in a volatile or a non-volatile memory device. The specimen may be provided for scanning on a solid support, such as a circular disc. The objects may be cells or microorganisms of a particular rare type i.e. they may be present in a very low density in the specimen.

BACKGROUND OF THE INVENTION

In U.S. Pat. No. 5,374,989 an apparatus for identifying an object having a non-specific outer boundary is disclosed. The apparatus comprises a tracking device for tracking a position of the object to be identified in two dimensions and an identification device for identification of the tracked object. The objects to be identified may be stained so as to distinguish them from other objects by a difference in transmissivity at a specific range of wavelengths. The object identification device comprises a coherent light source illuminating an area of the specimen and a detection device with a plurality of circular coaxial sections which are detecting the intensity distribution of a Fourier transform of light transmitted through the objects of the specimen.

U.S. Pat. No. 5,663,057 discloses an apparatus and a process for rapid counting of fluorescent microorganisms in a specimen. A solid support, such as a filter, holding the fluorescent microorganisms is scanned line by line with a laser beam having a circular focus area, with a diameter between 4 and 14 µm, on the filter. The emitted fluorescence is measured at one or more predetermined wavelengths. The scanning lines on the filter are produced in an overlapping pattern, and line-to line features are compared in time synchrony to eliminate uncorrelated events like random noise etc. A digital signal processing circuit applies a set of predetermined mathematical algorithms to the obtained fluorescent light signals to avoid or minimise detection of false positive responses and false negative responses.

The above mentioned types of prior art apparatuses utilises a Cartesian (x,y) scanning and tracking methodology, whereby the specimen is scanned line by line and the particular type of objects are recognised by either detecting emitted light from the objects or by detecting characteristic parameters of an optical Fourier transformation of light transmitted through the object.

These prior art methods of scanning specimens to locate the objects are too slow for practical purposes when the particular type of objects or target objects are very rare in the specimen, i.e. they may have a density of 1E-6 or less. The slowly scanning is due to the Cartesian scanning of the specimen and the small focus area of the utilised laser beams combined with the large number of objects, which have to be analysed before it is likely that a target object is located and identified. Further, due to the limited dimensions of the specimen provided by these prior art methods, it may not contain any target objects at all.

SUMMARY OF THE INVENTION

Accordingly, it is an object of the present invention to provide a method and apparatus which are capable of rapid scanning of large area specimens and, simultaneously, capable of detecting positions of target objects within the specimen.

It is also an object of the present invention to provide an apparatus, which may store the positions of the detected target objects in a volatile or a non-volatile memory device. The positions of the detected target objects may subsequently be retrieved from the memory device, and the objects may be subjected to a thorough analysis in order to establish their identity.

An apparatus according to the present invention may provide a solid support, adapted to receive and hold the specimen, with an area at least twenty times larger than the at most 400 mm$^2$, utilised in prior art apparatuses.

The apparatus may also be adapted to provide rapid scanning of specimens provided on slides of standard sizes such specimens are commonly used in microscopy in the medical field.

The large area of the specimen that may be scanned by the present apparatus is a significant advantage, especially in applications involving detection of very rare target objects, since a substantially larger number of target objects are likely to be present in the specimen than the number of target objects provided by prior art apparatuses.

It is further an advantage of the present invention that it may utilise a light source capable of irradiating, on the specimen, a focus area substantially larger than focus areas provided by prior art apparatuses. The large focus area, which may be provided by an embodiment of the present apparatus, enables rapid scanning of even very large specimens.

According to a first aspect of the invention there is provided an apparatus for detecting a property of an object contained in a specimen, the apparatus comprising
a frame, a member positioned on the frame and having a surface that is adapted to receive and hold the specimen, a detector for detection of the property of the object, and scanning means for scanning the specimen in relation to the detector along a non-linear curve.

The member may, further, be positioned for rotation about an axis on the frame and the scanning means comprise means for rotating the member about the axis.

The apparatus may further comprise scanning control means for controlling the scanning means to scan the specimen along a predetermined curve, such as a substantially circular curve.

According to a preferred embodiment of the invention, the apparatus comprises storage means for storage of a detector signal provided by the detector and one or several corresponding position signals provided by the scanning control means. This embodiment of the apparatus preferably also comprises means for sampling and digitising the detector signal and the corresponding position signal(s).

The apparatus may further comprise signal processing means operationally connected to the detector and adapted to receive and process the detector signal to detect a presence of an object or a particular type of target object or objects. The corresponding position signal(s) associated with any detected objects may subsequently be stored in the storage means.

The apparatus is preferably adapted to be capable of scanning specimens that have areas larger than 500 mm², or more preferably larger than 2000 mm², or even more preferably larger than 8000 mm².

In one embodiment of the invention, a magnetic property of the target objects is provided for the target objects in the specimen. This can be accomplished by staining the target objets with a magnetic marker. When the specimen is scanned with a magnetic sensitive detector, such as a magnetic reading head, the target object(s) and their positions may be detected by recording an electrical output signal of the reading head and the corresponding position signal(s).

In another embodiment of the invention, the target objects are stained with a fluorescent marker and a light source is also provided emitting a first light beam towards the specimen. Further, a light sensitive detector may be provided in this embodiment to detect emitted light from the target object or objects upon interaction with the first light beam during the scanning of the specimen.

In embodiments of the apparatus that utilise the light source, the scanning of the specimen may be performed according to anyone of at least three different methodologies. Each of these scan methodologies may correspond to a particular embodiment of the invention, as detailed below.

In a first and preferred embodiment of the present apparatus, the member is positioned on the frame of the apparatus. The light source may emit the first light beam towards the specimen, preferably provided on a disc, and the scanning means may be adapted to scan the light beam across the specimen along the non-linear curve. The detector is adapted to detect light emitted from objects comprised in the specimen upon interaction with the first light beam during scanning of the specimen. The member is furthermore positioned for rotation about an axis of the apparatus frame. The scanning means may comprise a DC motor and a spindle rigidly connected to the DC motor. The spindle may, further, be connected to the member which may be a substantially circular disc, holding the specimen to allow the specimen to be rotated about the axis of the apparatus frame.

The scanning means may also comprise deflecting means that may comprise a servo motor or a stepper motor connected to the member holding the specimen and thereby adapted to scan the first light beam along a radius of the circular movement of the disc holding the specimen.

According to another, second, embodiment of the invention, the member holding the specimen is stationary relative to the apparatus frame during the scanning. The light source is positioned for rotation about the axis on the frame and the scanning means may comprise means, which are adapted to rotate the light source about this axis of the frame. The scanning means may, further, comprise deflecting means adapted to scan the first light beam across the specimen along a radius of the circular movement of the light source. This second embodiment is particularly advantageous if the specimen comprising the objects is provided in an unstable e.g. fluid physical state such as in a liquid nutritional solution that allows the target objects to multiply prior to the scanning. This second embodiment of the invention supports scanning of such fluid specimen without the risk of shifting positions of objects in the specimen, since the objects are relived from centripetal forces produced by rotating the specimen.

According to a third and yet other embodiment of the invention, the light source emitting the first beam and the member holding the specimen may be stationary relative to the apparatus frame during the scanning. Instead moveable deflecting means, which may comprise a mirror, may be provided to rotate around a first axis, thereby enabling the first light beam to be scanned across the specimen along a substantially circular curve. The moveable mirror may further be rotatable around a second axis to vary the radius of the circular curve on the specimen so that the specimen may be scanned by the light beam along an e.g. Archimedes' spiral curve.

In the present specification and claims, "a non-linear curve" designates a curve, which can not be generated by any, finite, number of straight lines. Preferably, the non-linear curve is an Archimedes' spiral curve or a curve formed by a number of substantially concentric circular curves.

The target object or objects may be a particular type of biological cell(s), bacteria, micro-organisms, etc. as commonly of relevance in the medical field. In the medical field, these target cells or target micro-organisms may be found in specimens, which also comprise a large number of resembling cells or micro-organisms. These resembling cells or micro-organisms may constitute the main substance of the specimen, thereby being present in a much larger density than the density of the target cells.

The discrimination between the target object(s) and the objects of the main substance may be based on object differences of morphological, magnetic, or optical character.

The target objects are, preferably, stained by utilising antibody coupled magnetic beads or probes conjugated with fluorescent markers to provide them with the required difference from the objects of the main substance, and thereby serve as basis for the discrimination. Both types of antibody probes with fluorescent markers are today commercially available.

The objects may further be provided in a solution and the solution may be deposited on a substantially circular disc that may constitute the solid support adapted to hold the specimen.

An initial enrichment of the solution comprising the objects may be provided before the specimen is submitted for scanning. This initial enrichment may comprise the step of sorting the target objects from the objects of the main substance and/or the step of letting the target objects multiply (through reproduction), thereby enlarging the density of target objects in the specimen prior to scanning.

If a disc is used as the solid support holding the specimen, there exist, in principle, only few limitations to the disc size. Preferably, a disc diameter of approximately 120 mm, which is equal to the diameter of a CD, is utilised. This has several significant advantages, one advantage is that the effective area of a CD size disc is at least twenty times larger than the typical solid support area used in prior art apparatuses. Another advantage is that suitable mechanical and optical parts for the present apparatus may be found readily available and at a very low cost due to the wide spread use of CD based media. The disc may be manufactured in a transparent material, such as polycarbonate, glass, etc.

In a preferred embodiment, the detection of target objects is provided by scanning a first light beam across the specimen along a non-linear curve. This first light beam provides a light spot on the specimen, which irradiates the objects of the main substance together with any present target objects. The light beam may be provided by a monochromatic coherent light source, such as a semi-conductor laser, gas laser, solid state laser, etc. Alternatively, the light source could be of a type that emits broad-banded light. An optical filter may be inserted in the optical path between the light source and the specimen, so that a substantially monochromatic first light beam is emitted towards the specimen. The use of a broad-banded light source may render expensive laser devices superfluous, and still provide a substantially monochromatic light beam for illumination of the specimen.

The first light beam may comprise light having spectral components at more than a substantially single wavelength. Such a first light beam may be provided by a laser source which is capable of simultaneously generating light components of at least two different wavelengths. Alternatively, a "multi-wavelength" first light beam may be produced by a broad-banded light source combined with a number of optical components inserted in the optical path between the source and the specimen. This last solution may, however, be too complex for practical use.

In a preferred embodiment of the invention, the first light beam is generated by a 488 nm argon-ion gas laser. The target objects in the specimen are, further, stained with at least one fluorescent marker to differentiate them from the objects of the main substance. The specimen is, preferably, dispersed on a disc surface having a diameter of, approximately, 120 mm. The laser beam is focused into a circular spot on the specimen during the scanning. The spot diameter is, preferably, between 20-150 µm, more preferably between 20-80 µm and even more preferably between 30-60 µm. Preferably, the spot diameter is adapted to a particular application so that an optimum signal to noise ratio is provided in the detector signal, thereby enhancing the discrimination between target objects and false positive signals. These false positive signals may originate from random noise in the detector and its associated electronic circuitry, or they may originate from autofluorescent objects and particles, which may have contaminated the specimen.

It may be desirable to utilise the largest possible spot diameter in the present apparatus to minimise the scan time of the specimen. Several practical limitations may, however, restrict the maximum possible spot diameter for a particular application. One limitation, in applications involving the detection of fluorescent target objects, may be that a large spot diameter also tends to illuminate a large number of fluorescent contaminated objects and particles. These objects and particles may provide emitted light of intensity larger than the intensity provided by an illuminated target object, thereby deteriorating the discrimination between target objects and other objects of the specimen or even completely preventing the detection of a target object.

The maximum light power available from the light source may provide another limitation to the maximum spot size that can be used. However, in a preferred embodiment of the present apparatus, which utilises a laser light source, this potential limitation has not yet been of serious concern.

Thus, an apparatus according to the present invention may be adapted to identify several types of objects, in a variety of applications, with optimum speed and reliability.

Fluorescent light may be emitted from the target objects during scanning when the first light beam irradiates the target objects and their surroundings. The resultant light, produced by the interaction between the objects of the specimen and the first light beam, may comprise an emitted fluorescent light component from the target objects and a component originating from the first light beam. The resultant light may either be transmitted through the disc surface, reflected from the disc surface, or simultaneously reflected and transmitted. Accordingly, the resultant light may be detected either above the disc surface or below the disc surface when the disc is provided in a transparent material.

The detector is naturally selected so that it is sensitive to the property difference between the target objects and objects of the main substance, this property difference being of morphological, magnetic, optical, etc. character.

In embodiments of the invention where the specimen is scanned by a light source, a light sensitive detector may, obviously, be selected. Several types of devices may be utilised such as CCD devices, photo-transistors, photo-multipliers, etc. depending upon the requirements of a particular application. In a preferred embodiment of the invention, a photo-multiplier is used as a light detector. This type of detector may produce an electrical output signal substantially proportional to the light intensity striking it. The electrical output signal of the detector may, further, be provided to storage means adapted to store the detector signal together with one or several corresponding position signals provided by the scanning control means, which additionally may be comprised in the present apparatus.

Means may, further, be provided for sampling, digitising and storing one or several electrical signals that may be generated by the at least one detector, such as a photo-multiplier, and the corresponding position signal(s) provided by the scanning control means. Accordingly, each time an object is detected, a corresponding coherent data set may be stored in the storage means, and each of the coherent data sets may be seen as representing a unique signal "event".

The coherent data sets may thus represent a number of digitised detector and position signals, the number depending upon the utilised number of detectors and the number of signals provided by the scanning control means. Each of these digitised detector and position signals is, preferably, represented by a series of digital samples generated by one or several A/D-converters. Thereby, each unique signal "event" detected during the scanning of the specimen, and which may or may not originate from a target object, may be represented by a stored coherent data set. Signal "events" not originating from target objects may originate from random noise in the detector and its associated electronic circuitry, or may originate from autofluorescent objects and particles that may have contaminated the specimen as previously explained. These last mentioned signal "events" are denoted false positive signals in the following.

In a preferred embodiment of the invention, a substantially rectangular slit is formed in a (non-transparent) mask inserted in the optical path from the specimen to the photo-multiplier. The photo-multiplier accordingly "sees" the irradiated part of the specimen through a rectangular aperture. The slit or aperture may be placed with its longest side (the length) in parallel with a radius of the circular solid support holding the specimen.

The dimensions of the aperture are, preferably, adapted to the dimensions of the target objects to be detected and located, in such a manner that the width of the aperture is approximately equal to the dimensions of the target objects and the length is approximately equal to 3-5 times the target objects' dimensions, as projected on the specimen. As projected meaning that the dimensions of the aperture should be adapted to any magnification/demagnification provided in the optical path between the specimen and the aperture.

Further, the laser spot irradiating the specimen is, preferably, provided with a diameter approximately equal to the aperture length.

For example, in an embodiment of the invention wherein the target objects have dimensions of approximately 10 µm, an aperture length of 30-50 µm and an aperture width of between 7.5-15 µm may be selected.

One advantage of applying the aperture in the optical path is that e.g. fluorescent target objects "appearing" within the aperture boundaries at the detector and irradiated by the first light beam, will generate maximum signal level in the detector output signal only during that short instant in time where the target object is fully within the boundaries of the aperture. Consequently, it is possible to detect a very accurate value for the angular co-ordinate of the target object since the detector signal is not smeared by the target object travelling along a prolonged illumination path.

Another advantage is that the aperture may enhance the achievable discrimination between target objects and objects generating false positive signals due to a difference in size between these object groups. A "large" object, i.e. an object having dimensions larger than the aperture width, and which therefore can not belong to the group of target objects may erroneously have been stained with a fluorescent marker and thus emits light when irradiated by the first light beam. However, such a large object will generate maximum signal strength from the detector during a longer time interval than the target objects, due to a longer time of "visibility" or appearance within the boundaries of the aperture. This difference in signal duration which originates from the size difference between detected objects of the different groups, may be used as a basis for discrimination between target objects and other objects in the specimen, and thus enhance the detection of target objects.

Further, the specimen may be scanned, along a radius of the disc holding the specimen, by advancing the position of the aperture and the position of the light spot relative to the specimen with equally large steps i.e. tracking each other. Preferably, the steps have a size of 0.5-1.5 times the dimensions of the target objects. By scanning the first light beam across the specimen according to that method, a pattern of partially overlapping concentric circular curves is produced on the specimen. The overlap of the scan curves will make a particular target object "appear" at least 2-3 times at the photo-multiplier at a constant rectangular co-ordinate, but at slightly different radial co-ordinates of the aperture. Thereby 2-3 corresponding coherent data sets may be obtained, each set corresponding to electrical signals from the photo-multiplier and the scanning control means.

Signal processing means may subsequently retrieve and use these corresponding coherent data sets to enhance the discrimination between signals originating from target objects and false positive signals. This discrimination may be achieved by analysis of correlation between data sets originating at identical angular co-ordinates but at adjacent radial co-ordinates of the aperture.

When the rectangular aperture is used, an elliptical light spot shape on the specimen may, preferably, cover the entire length of the aperture. The elliptical spot shape may be advantageous since it provides a larger light power within the aperture boundaries than a circular spot, for a fixed light power radiated by the source.

The detection of target objects may be enhanced by inserting one or several optical filters in the light path between the specimen and the detector to attenuate the source light component of the resultant light before it is transmitted to the detector. Preferably, at least one optical filter, preferably a dichroic filter, is inserted in this light path.

The target objects may be stained with different types of fluorescent markers. Preferred marker(s) may be selected according to their optimum excitation light wavelengths and/or their quantum efficiencies. Since, usually, only a particular part of the light spectrum is useful for excitation of a particular type of fluorescent marker, a light source capable of providing light of a sufficiently high intensity relatively close to the optimum excitation wavelength of the marker should be selected.

Further, the target objects may be stained with two or more different fluorescent markers so that the target objects may provide emitted light at several wavelengths when they are irradiated by source light of appropriate spectral distribution. This distribution may be provided by the light source, so that it only provides substantial light intensity at wavelengths located close to an excitation wavelength of a marker.

When the target objects are stained with two or more fluorescent markers, target objects in the specimen may be detected by performing successive scans of the specimen, a method hereby denoted "multiple pass scan". The light wavelength of the source may be, during each scan, adapted to excite a particular marker on the objects. The bandwidth of optical filters inserted in the light path between the specimen and the detector may also be adapted to transmit only the wavelength range emitted by the particular fluorescent marker currently being excited by the source light during the scanning.

Alternatively, target objects may be detected in a "single pass scan" of the specimen even though the target objects are provided with e.g. two different markers. This may be achieved by simultaneously exciting both markers with a substantially monochromatic light beam, if the optimum excitation wavelengths of the markers are located sufficiently close in the light spectrum. Light emitted from the target objects may then comprise a light component from each of the markers, and the component originating from each marker may be detected by a separate detector provided for each of the markers. At least one optical filter may be inserted in each optical path from the specimen to the detector. Each filter being adapted to transmit to the detector only light emitted from a particular marker.

Utilising several markers may be advantageous to locate a particular type of target objects possessing several characteristics, and where each characteristic makes the target objects capable of binding a particular type of marker. This type of target objects may be detected and located by, during a first scan of the specimen, locate a first group of objects, which have been stained with a first type of marker, and subsequently during a second scan locate a second group of objects that have been stained with a second type of marker. By determining the intersection of the two groups, e.g. by utilising the signal processing means, the target objects may be identified. Of course, more than two types of markers may be utilised for staining the target objects depending on the particular application and on the number of characteristics of the target objects that have the ability to bind a particular marker.

An important application area, illustrating the importance of the binding of different markers to different object characteristics, is provided by the medical field. Detection and analysis of fetal cells from maternal blood provide a very low risk invasive alternative to prenatal diagnostic procedures, such as amniocentesis of chorionic villus sampling. To provide this analysis, at least one fetal cell with a nucleus must be located in a specimen.

The specimen may, further, comprise both maternal cells and fetal cells, and both types may be present with or without a cell nucleus. The detection and location of fetal cells with cell nucleuses may be accomplished by utilising a first fluorescent marker conjugated to a probe, such as an oligonucleotide, which is in situ hybridized to mRNA for gamma globin at least at a part of the fetal cells, and utilise a second fluorescent marker, preferably, DAPI or PI that binds to all cell nucleuses.

By scanning the specimen a first time to locate cells stained with the first fluorescent marker and thus belonging to a first group, and a second time to locate cells stained with the second fluorescent marker, the intersection of the cells groups will contain the target cell(s), i.e. fetal cells that also have a nucleus.

Utilising at least two different markers may also be advantageous to enhance the discrimination between false positive signals and signals originating from target objects during or after the scanning of a specimen. The discrimination may be enhanced in a "multiple pass scan" where the specimen may be scanned in a first pass with light adapted to excite a first marker. Coherent data sets obtained during the scanning, which may correspond to detected objects are stored in the memory. Subsequently the specimen may be scanned a second time with light adapted to excite a second marker and the coherent data sets associated with the detected objects may also be stored in the memory. The discrimination may subsequently be provided by comparing signal values from the detector, obtained at identical angular and radial co-ordinates on the specimen, in the two data sets. One criteria for accepting a detector signal as originating from a target object may be that only signals values, in both data sets, larger than a predetermined threshold value are accepted as originating from a target object. Accordingly, signal values above the threshold in only one of the two data sets may be discarded as originating from noise, autofluorescent particles, etc. and thus being false positive. Identical criteria may, naturally, also be used for discrimination between false positive and "true" detector signals as obtained during a "single pass scan" of the specimen.

A fluorescent marker should, preferably, posses a large quantum efficiency at one hand, and at the other hand posses a large difference between the optimum wavelength of excitation light and the optimum wavelength of emission light.

Preferably, Fluorescein or Fluorescein derivatives may be used as a fluorescent marker(s), since these substances are well known, readily available and possess large quantum efficiencies. Further, optimum wavelengths for excitation light and for emission light are located at 505 nm and 516 nm, respectively, for Fluorescein, which makes it possible to excite this substance by a preferred light source, a 488 nm argon-ion gas laser.

The storage means may be located in a personal computer (PC), which is operationally connected with the apparatus of the present invention. The storage means may comprise magnetic, optic or electric storage media, such as hard disc drives, DAT-tapes, floppy discs, CD-ROM discs, EEPROMs, etc. which may be utilised for non-volatile storage of the coherent data sets obtained from the scanning of the specimen(s). The storage means may also comprise intermediate volatile storage means, preferably RAM, to store coherent data sets during the scanning. This may be advantageous in applications where the data rate provided by the ND converter(s) is/are higher than the maximum storage rate accommodated by a non-volatile type of memory device.

The storage means may, alternatively, be provided inside the frame of the apparatus in one embodiment of the present invention, thereby providing a convenient portable "stand alone" apparatus.

It some situations, it may be desirable to identify detected target objects after a specimen has been scanned. According to a preferred embodiment of the invention, this is accomplished by retrieving coherent data sets, corresponding to detected target objects, from the memory device. Since these coherent data sets contain information related to the position (s) on the specimen (i.e. may be angular and radial co-ordinates) of the selected target objects, the scanning control means may be adapted to place an automated microscope at the position of any desired target object. Thereby, a medical doctor or a laboratory technician is capable of performing a detailed examination of the target object to e.g. establish its identity.

According to a second aspect of the invention there is provided a method of detecting a property of an object contained in a specimen and comprising the steps of positioning the specimen on a member having a surface that is adapted to receive and hold the specimen,
scanning the specimen in relation to the detector along a non-linear curve, and
detecting the property of the object during scanning of the specimen.

The method may further comprise the step of rotating the member holding the specimen about an axis.

According to a preferred embodiment, the method furthermore comprises the step of storing detector signals relating to the detected property and storing corresponding position signals relating to the current position of the member. Preferably, the method further comprises the steps of sampling, digitising and storing these detector and position signals are as coherent data sets in a memory device.

BRIEF DESCRIPTION OF THE DRAWING

FIG. 1 shows an embodiment of an apparatus according to the invention including components provided in an optical path.

DETAILED DESCRIPTION OF A PREFERRED EMBODIMENT

FIG. 1 shows a preferred embodiment of an apparatus according to the invention, adapted to scan large a specimen 14. A member 17 positioned on a frame (not shown) may hold a substantially circular disc 13 with a diameter of 120 mm, the disc providing a specimen 14, which is submitted for scanning. Furthermore, a microscope 20 is provided for examination of the specimen.

The specimen may comprise material originating from a blood or tissue sample from a pregnant woman. The specimen may comprise both adult cells and fetal cells, which may be analysed as a part of a prenatal diagnostic procedure. Accordingly, in the present embodiment of the invention, it is highly desirable to detect and determine positions of fetal cells and in particular fetal cells having a cell nucleus so that an analysis of the chromosomes in the cell nucleus may be provided. Accordingly, target cells in the present application are those fetal cells that comprise a cell nucleus.

However, it is today believed in the medical community that these fetal cells may have a density as small as 1E-9-1E-5 in the specimen, and they may be present in as little as 50% of the population of pregnant women. This very low density makes it necessary to perform a rapid scanning of the specimen if the fetal cells are to be located in a reasonable amount of time.

In order to locate the fetal target cells in the specimen, they are, preferably, stained with Fluorescein or Fluorescein derivative markers.

Preferably, a coherent first light beam 12, from a 488 nm argon-ion gas laser (not shown) is emitted towards the specimen 14 creating an approximately 40 μm diameter laser spot on the specimen 14. The specimen 14 is scanned by this laser spot along a non-linear curve under the control of scanning means 18 comprising DC motor (not shown) and scanning control means (not shown).

The DC motor, which may be directly connected to the member 17 holding the disc 13 through spindle 19, provides a drive mechanism that enables the disc 13 to be rotated about an axis on the frame. The DC motor further comprises an angle encoder (not shown) capable of providing a signal related to the current angular co-ordinate of the member 17 and the disc 13 to the scanning control means. The angular resolution of the angle encoder is, preferably, $$\theta_0 = \frac{360}{20000} = 0.018 \text{ Degrees}.$$

The rotational speed of the disc 13 is, preferably, adjusted to be within the interval from 200 to 1500 rpm. The scanning control means may comprise servo means adapted control the rpm of the disc, to produce a substantially constant linear velocity of the laser spot on the disc surface, a principle well known from CD players.

Deflecting means, which form part of the scanning means, and comprise a stepper motor (not shown), are further provided so the disc 13 with the specimen 14 may be displaced along a radius of the disc and its circular movement. Thereby providing a scan of the entire surface area of the disc 13 with the specimen 14 by the laser spot. When the deflecting means moves the disc 13 with the specimen along the radius, a non-linear curve comprising a number of concentric partly overlapping circular curves is formed on the disc 13 surface by the laser spot.

The optical system of the apparatus comprises a 488 nm argon-ion gas laser (not shown) used as a light source. The first light beam 12 emitted from the laser is transmitted through a focusing lens 10 and a dichroic filter 9 to dichroic beam-splitter 6. This beam-splitter 6 serves two purposes, first to reflect the first light beam 12 towards the specimen 14, and second to filter and direct resultant light 15 emitted from the specimen 14 towards a photo-multiplier 1. The resultant light 15 may comprise a light component originating from a reflected portion of the first light beam 12 and a fluorescent light component emitted from fluorescent target objects (not shown) contained in the specimen 14. The dichroic beam-splitter 6 and the dichroic filter 4 both contribute to attenuate the light component originating from the laser source (not shown), thereby enhancing the signal to noise ratio of light transmitted to the photo-multiplier 1. The resultant light 15 passing dichroic filter 4 is transmitted through a rectangular slit 16 provided in a mask 3 inserted in the optical path to the photo-multiplier 1. The slit 16 is, preferably, provided with dimensions that result in projected dimensions of length 30 µm and width 15 µm, respectively on the photo-multiplier 1. Accordingly, the slit 16 creates a light path aperture of dimensions, which combined with magnification lens 11, and the optical system comprising lenses 2, 5 and 7, defines the dimensions of the irradiated part of the specimen as "seen" by the photo-multiplier i.e. the dimensions of the irradiated specimen area projected upon the photo-multiplier 1.

The invention claimed is:

1. An apparatus for identifying a position of marked objects having unknown positions and detecting a property of the marked objects contained in a specimen, wherein the marked objects are marked with a fluorescent stain, the apparatus comprising
a frame,
a member positioned on the frame and having a surface that is adapted to receive and hold the specimen,
at least a first light source for emitting at least a first light beam towards the specimen held by the member, wherein the first light beam is adapted to provide a light spot having a diameter between 20-150 µm on the specimen,
at least a detector for detecting fluorescent light emitted from the marked objects upon interaction with the first light beam, the first light source and the detector being arranged so that a part of a light beam path from the first light source to the specimen is co-axial with a part of the light emitted from the marked objects,
at least one beam-splitter being arranged to reflect the first light beam towards the specimen and filter light emitted from the specimen, thereby allowing fluorescent light from the marked objects to pass through the beam-splitter to the detector,
scanning means for scanning the entire surface of the member in relation to the detector along a non-linear curve, wherein the scanning means comprises means for rotating the member and means for displacing the member along a radius of the rotation of the member, so as to identify the position of the marked objects in the entire specimen and detect the property of the marked objects, the means for rotating and the means for displacing being directly connected to the member, the member being rotatable and displaceable along a radius of the rotation of the member,
scanning control means for controlling the scanning means for scanning the specimen along the non-linear curve,
storage means for storing detector signals relating to the marked objects provided by the detector and corresponding position signals provided by the scanning control means,
means for retrieving the position signals stored in the storage means, and
a microscope for viewing images of the marked objects, wherein the scanning control means use the retrieved position signals to place the microscope at the position of the marked objects to allow performing a detailed examination of the marked objects.

2. An apparatus according to claim 1, wherein the member is positioned for rotation about an axis on the frame and wherein the means for rotating the member rotates the member about the axis.

3. An apparatus according to claim 1, wherein the scanning control means are adapted to control the scanning means in such a way that the non-linear curve is a substantially circular curve.

4. An apparatus according to claim 1, further comprising means for sampling and digitising the detector signals and the position signals.

5. An apparatus according to claim 1, further comprising signal processing means operatively connected to the detector to detect a presence of an object based on the detector signals.

6. An apparatus according to claim 1, wherein the specimen has an area larger than 500 mm$^2$.

7. An apparatus according to claim 1, wherein the specimen has an area larger than 8000 mm$^2$.

8. An apparatus according to claim 1, wherein a mask is inserted in an optical path between the specimen and the detector, and the mask comprises at least one transparent aperture.

9. An apparatus according to claim 8, wherein the aperture shape is a substantially rectangular shape.

10. An apparatus according to claim 1, wherein the first light source is a coherent light source.

11. An apparatus according to claim 1, wherein the detector comprises a CCD device.

12. An apparatus according to claim 1, wherein the position signals of the marked objects are angular and radial coordinates.

13. A method of identifying a position of a fluorescently marked object having an unknown position and detecting a property of the object contained in a specimen, wherein the object is a biological cell or a microorganism, the method comprising the steps of:
- positioning the specimen on a member having a surface that is adapted to receive and hold the specimen,
- emitting at least a first light beam from a first light source towards the specimen held by the member, wherein the first light beam is adapted to provide a light spot having a diameter between 20-150 µm on the specimen, and wherein the first light beam is reflected by a beam-splitter towards the specimen,
- scanning the entire surface of the member in relation to a detector along a non-linear curve by rotating the member holding the specimen and displacing the member along a radius of the rotation of the member, the member being rotatable and displaceable along a radius of the rotation of the member,
- arranging the light source and the detector, so that a part of a light beam path from the first light source to the specimen is co-axial with a part of a light emitted from the object,
- filtering through said beam-splitter light emitted from the specimen, passing fluorescent light from the marked objects through the beam-splitter towards the detector,
- detecting the fluorescent light emitted from the object, thereby identifying the position of the object and detecting the property of the object during scanning of the entire specimen,
- storing detector signals relating to the object provided by the detector and corresponding position signals provided by the scanning control means,
- retrieving the position signals stored in the storage means,
- placing a microscope at the position of the object using the retrieved the position signals to allow performing a detailed examination of the object, and
- optically inspecting the object by viewing an image of the object via the microscope by a user.

14. A method according to claim 13, further comprising the step of storing signals relating to the detected property and corresponding data relating to the current position of the member.

15. A method according to claim 14, further comprising the step of sampling and digitising the signals and the data.

16. A method according to claim 13, further comprising establishing identity of the object by viewing the image of the object.

17. A method according to claim 13, wherein the step of storing the corresponding position signals includes storing angular and radial coordinates of the object provided by the scanning control means.

18. A method according to claim 13, wherein the specimen has an area larger than 500 mm$^2$.

19. A method according to claim 13, wherein the specimen has an area larger than 8000 mm$^2$.

* * * * *